United States Patent [19]

Christensen et al.

[11] 4,146,633
[45] Mar. 27, 1979

[54] Δ³-THIENAMYCIN

[75] Inventors: Burton G. Christensen, Metuchen; Ronald W. Ratcliffe, Matawan; David H. Shih, Edison, all of N.J.

[73] Assignee: Merck & Co., Inc., Rahway, N.J.

[21] Appl. No.: 847,292

[22] Filed: Oct. 31, 1977

Related U.S. Application Data

[63] Continuation-in-part of Ser. No. 743,364, Nov. 19, 1976, abandoned.

[51] Int. Cl.² .................. C07D 487/04; A61K 31/40
[52] U.S. Cl. ............................... 424/274; 260/326.31
[58] Field of Search .................... 260/326.31; 424/274

[56] References Cited

U.S. PATENT DOCUMENTS 3,950,357  4/1976  Kahan et al. .................... 260/326.31

OTHER PUBLICATIONS

Flynn; *Cephalosporins and Penicillan* pp. 147–151 (1972).

*Primary Examiner*—Jose Tovar
*Assistant Examiner*—Mary C. Lee
*Attorney, Agent, or Firm*—Frank M. Mahon; James A. Arno; Julian S. Levitt

[57] ABSTRACT

The antibiotic Δ³-thienamycin is disclosed:

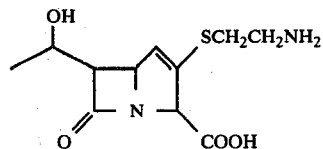

It is prepared by double bond isomerization of thienamycin. Also disclosed are pharmaceutical compositions comprising Δ³-thienamycin, and methods of treatment comprising administering Δ³-thienamycin when an antibiotic effect is indicated.

4 Claims, No Drawings

$\Delta^3$-THIENAMYCIN

BACKGROUND OF THE INVENTION

This application is a continuation-in-part of U.S. patent application Ser. No. 743,364, filed Nov. 19, 1976 now abandoned.

This invention relates to the new antibiotic $\Delta^3$ thienamycin (I) and its pharmaceutically acceptable salts:

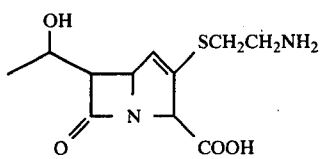

This invention also relates to processes for preparing I; pharmaceutical compositions comprising I and methods of treatment comprising administering I when an antibiotic effect is indicated.

$\Delta^3$-Thienamycin (I) is prepared from thienamycin (II) by isomerization of the double bond:

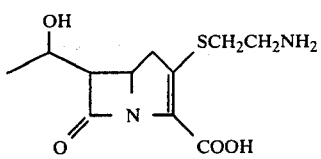

The $\Delta^3$-thienamycin compounds of the present invention (I) are also useful in the total synthesis of thienamycin and all its isomers as a reaction intermediate, which upon double bond isomerizations yields thienamycin (II). This invention also relates to O—, N— and/or carboxyl protected species of I:

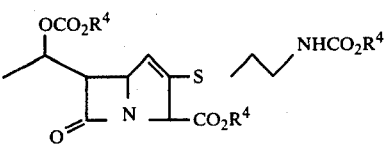

wherein $R^4$, in addition to H (or $CO_2R^4$ is H, i.e., free carbinol or amino functions), $R^4$ is selected from well-known, readily removable protecting groups, such as p-nitrobenzyl o-nitrobenzyl, t-butyl, 2,2,2-trichloroethyl, phthalyl and the like.

Thienamycin is disclosed and claimed in U.S. Pat. No. 3,950,357, issued Apr. 13, 1976, which patent is incorporated herein by reference since thienamycin may serve as a starting material for the preparation of the compounds of the present invention.

Thienamycin and all of its isomers (in pure form and as mixtures) are also obtainable by the total synthesis disclosed and claimed in copending, commonly assigned U.S. patent application Ser. No. 833,210 (Sept. 15, 1977). This application is incorporated herein by reference to the extent that it makes available all isomers of II as starting materials in the preparation of the compounds of the present invention (I).

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel antibiotic and the pharmaceutically acceptable salts thereof which are useful in animal and human therapy and in inanimate systems. These antibiotics are active against a broad range of pathogens which representatively include both gram positive bacteria such as *S. aureus, Strep. pyogenes* and *B. subtilis,* and gram negative bacteria such as *E. coli, Proteus morganii, Serratia* and *Klebsiella.* Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION $\Delta^3$-Thienamycin is conveniently prepared by the following reaction

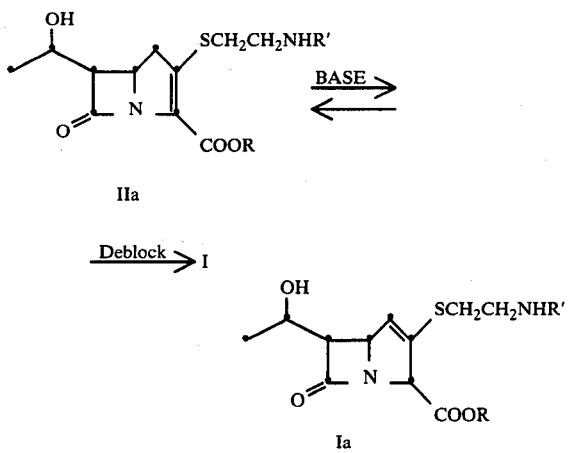

wherein R is a readily removable carboxyl blocking (or protecting group) and R' is a readily removable N-blocking group. Such blocked thienamycins, IIa, are disclosed in co-pending, commonly assigned U.S. patent application Ser. No. 634,006, filed Nov. 21, 1975; and its continuation-in-part U.S. patent application Ser. No. 733,655 filed Oct. 18, 1976 [Merck & Co., Inc. ]. Said applications are incorporated herein for its disclosure relative to the preparation of IIa. Preferred blocking groups R are benzyl and nuclear-substituted benzyl:

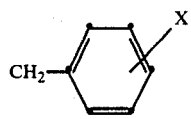

wherein X is nitro, methoxy, phenyl, and the like; benzyl is preferred. Suitable blocking groups R' include bromo-t-butoxycarbonyl, chloro-t-butoxycarbonyl, bromoethoxycarbonyl, benzyloxycarbonyl, p-nitrobenzyloxycarbonyl, and the like. An especially preferred N-blocking group is bromo-t-butoxycarbonyl.

In words relative to the above reaction diagram, a suitably protected thienamycin IIa is dissolved in a solvent such as dimethylsulfoxide (DMSO), dimethylformamide (DMF), tetrahydrofuran (THF), dioxane, hexamethylphosphoramide (HMPA), xylene, or the like. To this solution 0.05 to 3.0 equivalents of a base such as 1,5-diazabicyclo-[5.4.0]undec-5-ene (DBU), 1,5-diazabicyclo[3.4.0]non-5-ene (DBN), 1,4-diazabicylco[2.2.0]octane (DABCO)

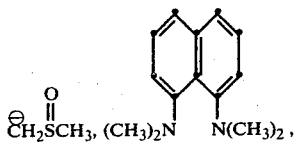

or the like is added. The mixture is allowed to reach equilibrium (2 to 60 minutes) at a temperature of from 0° to 80° C. The state of equilibrium is determined by ultraviolet absorption, or thin layer chromatography of sample aliquots. At equilibrium the base is removed by aqueous extraction and the desired product Ia, together with IIa, is extracted into a solvent such as ethyl acetate, chloroform, methylene chloride, ether or the like. The desired product is quantitatively separated by preparative chromatography, such as thin-layer chromatography on silica gel. Spectral characterizing parameters of the $\Delta^3$-thienamycin are given below. The deblocking (Ia →I) is conducted by any of a variety of well-known procedures such as hydrolysis or hydrogenation. Preferably, the carboxyl blocking group R is removed by hydrogenation in a solvent such as a lower alkanol, for example, ethanol, in the presence of a hydrogenation catalyst such as platinum, palladium or oxides thereof under 1 to 40 atmosphere of hydrogen. The N-protecting group R' may be removed by hydrogenation, but when the preferred bromo-t-butoxy-carbonyl group is used, the de-blocking is conveniently effected by heating a solution of Ia or carboxyl-deblocked Ia in a solvent such as ethanol, isopropanol, water, or the like at 25° to 80° C. for from 10 minutes to 3 hours.

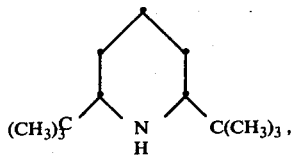

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as moncalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino-and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Salts of the primary amine of I with pharmaceutically acceptable organic and inorganic acids are also contemplated. Such salts include methanesulfonate, 2-naphthalenesulfonate, pamoate, 3-phenyl propionate, trimethylacetate, t-butyl acetate, p-toluenesulfonate, maleate, lactate, cyclamate, fumarate, tartrate, oxalate, benzoate, acetate, succinate, citrate, glutamate, hydrochloride, hydrobromide, sulfate, phosphate, n-acetylglycinate, benzenesulfonate, hexanoate, p-chlorobenzenesulfonate, cyclopentanepropionate, 1,2-ethane disulfonate, gluroheptanoate, ethanesulfonate, o-(4-hydroxybenzoyl)benzoate, 2-hydroxyethanesulfonate, and the like; and are prepared according to well-known procedures.

The salts can be mono-salts such as the mono- sodium salt obtained by treating one equivalent of sodium hydroxide with one equivalent of the product (I), also mixed di-salts. Such salts may be obtained by treating one equivalent of a base having a divalent cation, such as calcium hydroxide, with one equivalent of the product (I). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

$\Delta^3$-Thienamycin and salts thereof are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc., or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention.

EXAMPLE 1

Preparation of $\Delta^3$-N-Bromo-t-butoxycarbonyl thienamycin Benzyl Ester

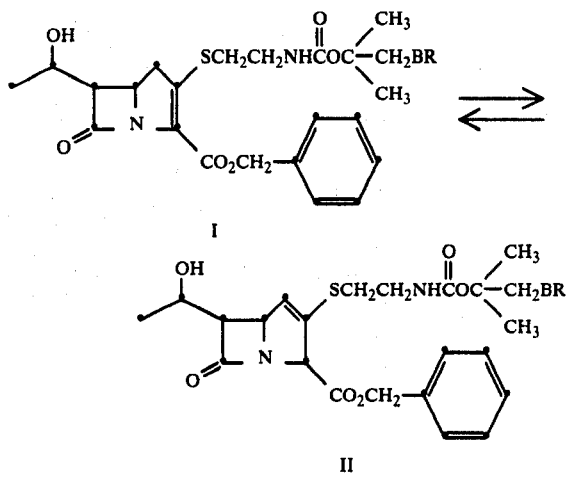

N-Bromo-t-butoxylcarbonyl thienamycin benzyl ester (I) (54 mg) is dissolved in 0.5 ml DMSO. To the solution is added 15μl of 1.5-diaza bicyclo[5.4.0]undec-5-ene (DBU) at 25° C. After the equilibrium between (I) and (II) is established (15–20 min.), the mixture is diluted with 5 ml ethyl acetate and washed with 2 ml water. The organic layer is separated, dried over Na$_2$SO$_4$ and concentrated to 0.5 ml. The crude products is subjected to TLC separation, (silica gel GF, ethyl acetate as solvent) which shows R$_f$ of 0.60 and 0.48 for $\Delta^3$ and $\Delta^2$-isomers, respectively. The desired product (II) (7.3 mg) is isolated and characterized by the following physical measurements.

uv $\lambda_{max}^{EtOH}$ 249 nm; ir (CDCl$_3$): 1773 1751 and 1718 cm$^{-1}$; Nmr (60 MHz, CDCl$_3$): δ1.32 (d, 3), 1.55 (s, 6), 2.90–3.50 (m,4), 3.77 (s,2), 4.20 (m,1), 4.63 (m,1), 5.12 (m,1), 5.20 (s,2), 5.98 (t,1) and 7.38 ppm (m,5).

EXAMPLE 2

Preparation of Δ³-N-Bromo-t-butoxycarbonyl thienamycin Sodium Salt (III)

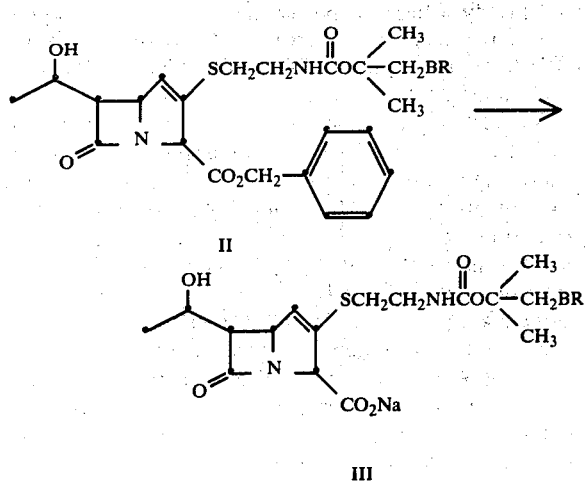

Δ³-N-Bromo-t-butoxylcarbonyl thienamycin benzyl ester (II) (20 mg) is dissolved in 4 ml. ethanol. To the solution is added 2 ml pH 8.0, 0.1M phosphate buffer and 60 mg of 10% Pd/C. The mixture is stirred under 1 atm of H₂ at 25° C. for 75 min, and then filtered from the catalyst. The filtrate is neutralized to pH 7.0 with 2.5 N HCl, concentrated to 3 ml and briefly extracted with 5 ml ether. The aqueous solution so obtained contains 90% of the partial deblocked product (III) and 10% of the complete de-blocked product, Δ³-thienamycin, as indicated by high pressure liquid chromatography (HPLC) [Bondapak $C_{18}$ reverse phase analytical column eluted with 10% THF in $H_2O$]. UV spectrum of the solution shows $\lambda_{max}^{H_2O}$ at 240 nm. Electrophoresis at 2KV in pH 7.0, 0.05 M phosphate buffer for 20 min displaces two bio-active zones with electrophoretic mobility of 30 mm toward the anode and 5 mm toward cathode which represent the partial de-blocked product (III) and the completely de-blocked product, Δ³-thienamycin, respectively.

EXAMPLE 3

Preparation of Δ³-Thienamycin

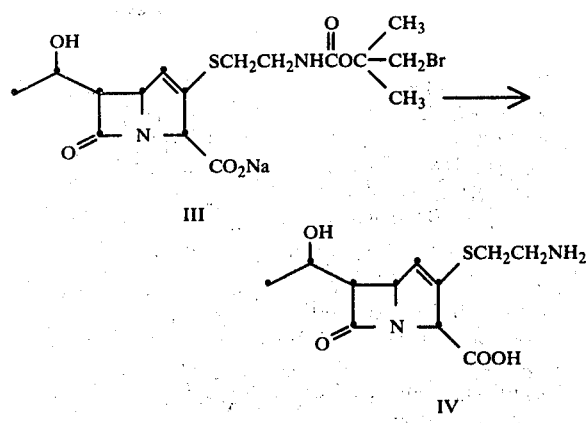

The solution obtained above, Example 2, which contains Δ³-N-bromo-t-butoxylcarbonyl thienamycin sodium salt III is heated at 60°–65° C. for 1 hr. HPLC analysis of the resulting solution shows the quantitative formation of IV. The mixture is chromatographed on a Dowex-50X8 (Na form) ion-exchange column (1.4 × 10 cm) which is eluted with water to give the desired product (IV) which shows UV $\lambda_{max}^{H_2O}$ 236 nm; single bioactive zone with electrophoretic mobility of 5 mm toward the cathode when the sample is analyzed at 2KV in 0.05 M, pH 7.0 phosphate buffer for 20 min, and single peak with retention time of 5 min on HPLC analysis ($C_{18}$ Bondapak reverse phase column, 0.2 × 61 cm, eluted with 10% THF H₂O at flow rate of 0.5 ml./min.).

EXAMPLE 4

Preparation of N-Bromo-t-Butyloxycarbonyl Thienamycin Sodium Salt

Method A: Thienamycin (190 mg) dissolved in 15 ml. 0.1M phosphate buffer and 15 ml dioxane is kept at 0° C. The solution is adjusted and maintained between pH 8.5–9.0 with 1N NaOH while 480 mg of bromo-t-butyl chloroformate is added to the solution during a period of 5 min. The mixture is stirred for 30 min, and then is neutralized to pH 7.0 with 1N HCl and extracted with ether. The aqueous layer is separated, concentrated to 10 ml and chromatographed on a Dowex-50X8 (Na Form) column (1.5" × 10") which is eluted with H₂O to give 113 mg of the desired product after lyophilization.

Method B: Thienamycin (95 mg) in 10 ml 0.1M phosphate buffer and 10 ml dioxane is kept at 0° C. The solution is adjusted and maintained between pH 8.5–9.0 while 240 mg of bromo-6-butyl chloroformate is added. The mixture is stirred for 30 min, and then is acidified to pH 2.0 with H₃PO₄. The acidified solution is extracted with 2×25 ml ethyl acetate. The organic layer is separated and back extracted with 10 ml of aqueous NaHCO₃ solution (solution contains 30 mg of NaHCO₃). The aqueous layer provides 30 mg of the desired product after lyophilization. NMR (60 MHz, D₂O): δ 1.26 (d), 1.60 (s), 2.65–3.50 (m), 3.70 (s), and 3.90–4.20 (m). UV $\lambda_{max}^{D_2O}$ 303 nm.

EXAMPLE 5

Preparation of N-Bromo-t-Butyloxycarbonyl thienamycin p-nitrobenzyl ester

The lyophilized N-bromo-t-butyloxycarbonyl thienamycin sodium salt (100 mg) is stirred at 26° C. with p-nitrobenzyl bromide (300 mg) in 2 ml hexamethylphosphoramide for 1 hr. The mixture is diluted with 10 ml ethyl acetate and then washed thoroughly with water. The organic layer is separated, dried over Na₂SO₄ and chromatographed on two 250μ silica gel GF TLC plates using ethyl acetate as solvent (R$_f$0.45) to give 50 mg of the desired product. IR (CDCl₃): 1777 (β-lactam) and 1711 cm⁻¹ (ester); UV $\lambda_{max}^{EtOH}$ 270 and 322 nm; Nmr (CDCl₃, 60 MHz): δ 1.38 (d), 1.58 mm (s), 2.60–3.80 (m), 3.78 (s), 3.90–4.20 (m), 5.30 (s), 7.55 (d) and 8.30 ppm (d).

The benzyl ester is obtained as above except an equivalent amount of benzyl bromide is substituted for the p-nitrobenzyl bromide of Example 5.

EXAMPLE 6

Preparation of Δ³-N-Benzyloxycarbonyl Thienamycin Benzyl Ester

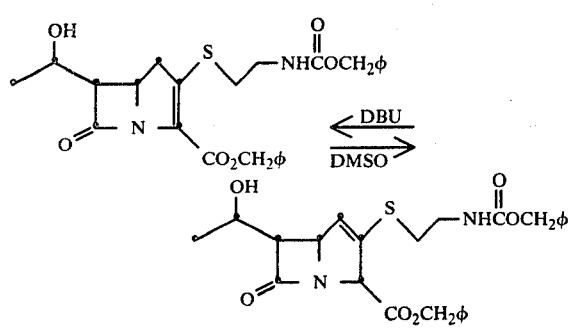

To a solution of N-benzyloxycarbonyl thienamycin benzyl ester (30 mg.) in anhydrous DMSO (200 μl) at 25° C. is added 1,5-diazabicyclo[5.4.0]undec-5-ene (10 μl). After standing at 25° C. for 10 min., the solution is diluted with Et₂O (8 ml), washed with H₂O (3 × 2 ml), 1M pH 3 phosphate buffer (1 ml), 5% aqueous NaHCO₃ (1 ml), and brine (2 ml), dried with MgSO₄, and filtered. Evaporation of the solvent in vacuo leaves a clear oil (20 mg.). This material is subjected to preparative tlc separation (0.25 mm × 20 × 20 cm silica gel GF plate, 3:1 EtOAc - CHCl₃ as developing solvent) which shows bands at Rf 0.39 and 0.54 for the Δ²- and Δ³-isomers, respectively. The Δ³- band is removed and eluted with EtOAc to yield the product (7.1 mg.) as a clear oil: ir (CHCl₃) 1770, 1745, and 1720 cm⁻¹; uv (dioxane) 223 and 247 (sh) nm; nmr (100 MHz, CHCl₃) δ 1.32 (d, 3, CH₃), 1.7 (br s, 1, OH), 2.91 (m, 2, SCH₂), 3.02 (d of d, H6), 3.36 (q, 2, CH₂N), 4.19 (p, 1, H8), 4.54 (d of d of d, 1, H5), 5.06 (d of d, H2), 5.04 (brs, 1, NH), 5.08 (s, 2, CH₂φ), 5.15 (s, 2, CH₂φ), 5.90 (t, 1, H4), and 7.31 (s, 10, φ): mass spectrum m/e 496 (M+), 478, 410, and 259.

EXAMPLE 7

Preparation of Δ³-N-p-Nitrobenzyloxycarbonyl Thienamycin p-Nitrobenzyl Ester

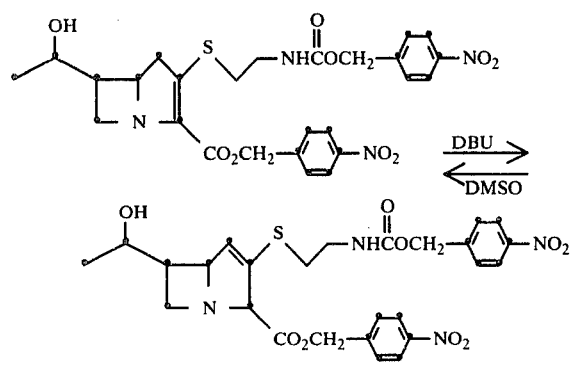

To a solution of N-p-nitrobenzyloxycarbonyl thienamycin p-nitrobenzyl ester (39 mg) in anhydrous DMSO (225 μl) at 25° C. is added 1,5-diazabicyclo[5.4.0]undec-5-ene (11 μl). After 10 mins at 25° C., the solution is diluted with EtOAc (10 ml), washed with H₂O (3 × 2 ml), 1M pH 3 phosphate buffer (1 ml), 5% NaHCO₃ (1 ml), and brine (2 ml), dried with MgSO₄, and filtered. Evaporation of the solvent in vacuo leaves a yellow semi-solid (35 mg.). This material is purified by preparative tlc on a 0.25 mm × 20 × 20 cm silica gel GF plate using 3:1 EtOAc - CHCl₃ as developing solvent. The band at Rf 0.44 is removed and eluted with EtOAc to give the desired Δ³-product (9 mg) as a pale yellow oil: ir (THF) 1772, 1749, and 1723 cm⁻¹; uv (dioxane) 241 (sh) and 269 nm; nmr (100 MHz, CDCl₃) δ 1.34 (d, 3, CH₃), 2.99 (m, 2, SCH₂), 3.08 (d of d, H6), 3.43 (m, 2, CH₂N), 4.25 (m, 1, H8), 4.59 (m, 1, H5), 5.15 (d of d, H2), 5.20 (s, 2, CH₂Ar), 5.28 (s, 2, CH₂Ar), 5.99 (m, 1, H4), and 7.85 (m, 8, ArH).

EXAMPLE 8

Preparation of Pharmaceutical Compositions

One such unit dosage form consists in mixing 120 mg of Δ³-thienamycin sodium salt with 20 mg. of lactose and 5 mg. of magnesium stearate and placing the 145 mg mixture into a No. 3 gelatin capsule. Similarly, by employing more of the active ingredient and less lactone, other dosage forms can be put up in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
|---|---|
| Δ³-thienamycin sodium salt | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| Δ³-thienamycin sodium salt | 500 mg. |
| diluent: sterile water for injection | 2 ml. |
| OPTHALMIC SOLUTION | |
| Δ³-thienamycin sodium salt | 100 mg. |
| Hydroxypropylmethyl cellulose | 5 mg. |
| Sterile Water | 1 ml. |
| OTIC SOLUTION | |
| Δ³-thienamycin sodium salt | 100 mg. |
| Benzalkonium Chloride | 0.1 mg. |
| Sterile Water | 1 ml. |
| TOPICAL OINTMENT | |
| Δ³-thienamycin sodium salt | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

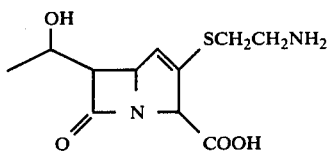

and its pharmaceutically acceptable salts.

2. A compound having the structural formula:

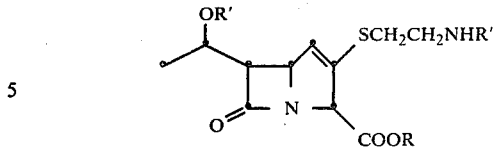

wherein R' is independently selected from hydrogen, bromo-t-butyloxycarbonyl, p-nitrobenzyloxycarbonyl, o-nitrobenzyloxycarbonyl, t-butyloxycarbonyl, or 2,2,2-trichloroethoxycarbonyl, and R is hydrogen, p-nitrobenzyl, o-nitrobenzyl, t-butyl, 2,2,2-trichloroethyl, or phthalyl.

3. An antibiotic pharmaceutical composition comprising a therapeutically effective amount of a compound according to claim 1 and a pharmaceutical carrier therefor.

4. An antibiotic pharmaceutical composition comprising, in unitary dosage form, a therapeutically effective amount of a compound according to claim 1 and a pharmaceutical carrier therefor.

* * * * *